United States Patent [19]

Huneidi

[11] 4,398,412

[45] Aug. 16, 1983

[54] DEVICE FOR DETERMINING FROST DEPTH AND DENSITY

[75] Inventor: Farouk Huneidi, Huntsville, Ala.

[73] Assignee: The United States of America as represented by the Administrator of the National Aeronautics and Space Administration, Washington, D.C.

[21] Appl. No.: 359,626

[22] Filed: Mar. 18, 1982

[51] Int. Cl.³ .............................................. G01N 9/00
[52] U.S. Cl. ................................ 73/32 R; 73/864.41; 73/150 R; 73/170 R; 33/169 F; 62/128
[58] Field of Search ............... 73/864.41, 32 R, 150 R, 73/170 R; 33/169 F; 62/128

[56] References Cited

U.S. PATENT DOCUMENTS

| | | | |
|---|---|---|---|
| 2,519,943 | 8/1950 | Tobey | 62/128 |
| 3,522,858 | 8/1970 | Christensen | 73/170 R X |
| 4,156,362 | 5/1979 | MacHattie et al. | 73/170 R X |
| 4,304,139 | 12/1981 | Johnson | 73/864.41 X |

FOREIGN PATENT DOCUMENTS

| | | | |
|---|---|---|---|
| 54-156588 | 12/1979 | Japan | 73/170 R |
| 468133 | 4/1975 | U.S.S.R. | 73/32 R |
| 763721 | 9/1980 | U.S.S.R. | 73/864.41 |

*Primary Examiner*—Steven L. Stephan
*Assistant Examiner*—Tom Noland
*Attorney, Agent, or Firm*—J. H. Beumer; J. R. Manning; L. D. Wofford, Jr.

[57] ABSTRACT

A hand held device (12) having a forward open window portion (14) adapted to be pushed downwardly into the frost on a surface, and a rear container portion (22) adapted to receive the frost removed from the window area. A graph (FIG. 4) on a side of the container enables an observer to determine the density of the frost from certain measurements noted. The depth of the frost is noted from calibrated lines (28) on the sides of the open window portion (14).

7 Claims, 4 Drawing Figures

DEVICE FOR DETERMINING FROST DEPTH AND DENSITY

DESCRIPTION

ORIGIN OF THE INVENTION

The invention described herein was made by an employee of the United States Government, and may be manufactured and used by or for the Government of the United States of America for Governmental purposes without the payment of any royalties thereon or therefor.

TECHNICAL FIELD

The invention relates to a device for determining the depth and density of frost, snow, and the like, and more particularly to a device suitable to establish the frost conditions on the external surface of a tank or pipes of large diameter filled with cryogenic liquid.

BACKGROUND ART

In handling of cryogenic liquids such as liquid hydrogen for spacecraft it is often necessary to determine the extent and seriousness of frost buildup on tanks and pipes holding the cryogenic fluid. This was accomplished herebefore by measuring a certain area of the surface of the frost, measuring the depth of the frost from within the certain area and weighing it, and then calculating the frost density. This prior technique was cumbersome because of the requirement of various tools and measuring devices which were confusing to the layman.

DISCLOSURE OF INVENTION

The present invention is a simple and practical hand held device which enables a quick determination to be made of the depth and density of the frost on the external surface of the tank pipe, or other object.

The device is a unitary body having a forward fixed area window defined by rectangular arranged sides which when placed against the frost surface and having downward pressure applied thereto sinks readily to the underlying supporting surface allowing the frost to occupy the open window space within the rectangular sides. Calibrated lines or scales are provided on the window sides to enable an observer to read the depth of the frost.

The rear portion of the unitary body is a container having a front entry opening adjacent and above the rear portion of the fixed area window. The frost occupying the space within the window is pushed or scraped backwards into the container through its entry opening. The container has calibrated lines along its upper side whereby when the frost melts, the height of the water therefrom may be easily read by an observer. A graph is applied to the lower side of the container which correlates for the user the depth of the frost and the height of the melt (water) to the density of the frost.

Accordingly, it is an object of the present invention to provide a device for quickly determining the depth and density of frost, snow, and the like on a surface.

Another object is to provide an easily manipulated device of a unitary construction for measuring the depth of frost, snow, and similar substances, and for quickly determining its density.

DETAILED DESCRIPTION OF THE INVENTION

Figure 1:
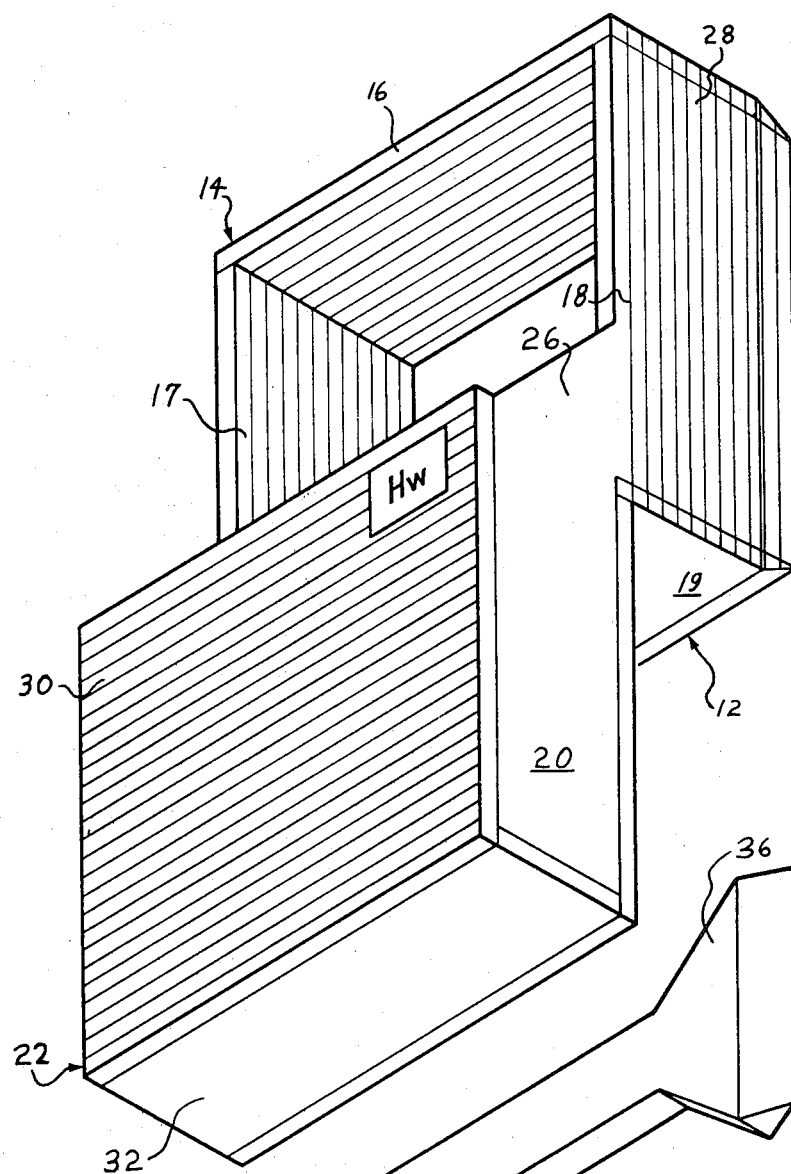
FIG. 1 is a pictorial view of a device for determining frost depth and density.

Referring to the drawings, there is shown in FIG. 1 a device 12 according to the present invention for measuring the depth of frost on an underlying supporting surface and for determining the frost density. While the device 12 will be described using terminology relative to its orientation of parts and use on a frost surface, such a lower, upper, and side, it should be understood that such terms are for ease of explanation and are not limiting to its orientation with regard to an observer or user of the device.

The device 12 as shown has a unitary body made of transparent hard plastic of about one-eight inch thick. As illustrated the body is made of various plates adhesively secured to abutting members. Obviously, the device 12 could be cast or parts thereof cast as a single piece so as to eliminate all or most of the joints formed by abutting members. The transparency of the plates of the body serves as an aid in its operation when making measurements.

The unitary body of the device 12 has a forward part 14 having four planar sides 16, 17, 18 and 19 arranged in a rectangular or square configuration so as to define an opening or window. The window sides 16, 17, 18 and 19 have a height greater than the anticipated depth of the frost to be measured, and the rear side 19 is slightly slanted outwardly from its lower to its upper edges as shown best in FIG. 3. Also, the lower parts of the window sides 16, 17, 18 and 19 are beveled along their outer rims to present a sharp lower edge.

The rear portion of the unitary body is a shallow rectangular container or collector 22 having its lower plate 24 joined to the rear window side 19 adjacent the upper edge of the side 19 so the container portion 22 presents a handle which is vertically offset from the front window portion 14 and parallel to the bottom edge of the window portion. The forward end 25 of the container 22 is open and above the rear side 19. The longitudinal vertical side plates 20 of the container have short triangular parts 26 to join with the upper edges of the corresponding longitudinal window sides 17, 18. The triangular parts 26 prevents the frost that is being manually shifted from the window opening into the container 21 from spilling over the ring sides 17, 18 as will be discussed, and also serves to strengthen the entire structural arrangement. Calibrated lines 28 one-eight inch apart are integrally grooved or etched on the outer vertical surface of the window sides 16, 17, 18 and 19 parallel to the rear plate 32 of the container 22 and measured from the forward surface of the rear plate 32.

Figure 3:
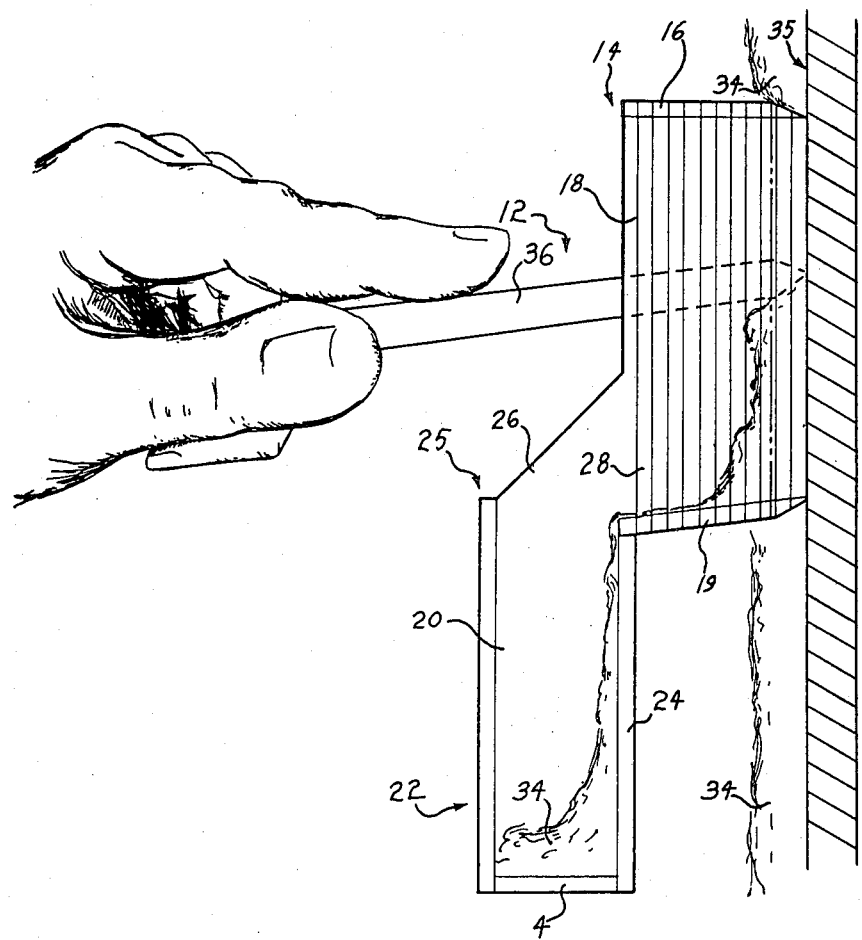
FIG. 3 is a side view of the device of FIG. 1 and scraper of FIG. 2 being utilized on a frost covered surface.

FIG. 3 illustrates the device placed on a frost covered surface 35. Initially, the device is placed against the upper surface of the frost 34 and the user applies a downward force to cause the front window portion 14 to slice through the frost 34 to the underlying supporting surface 35. The lower sharp edges of the window plate sides 16, 17, 18 and 19 allow the window portion to push through the frost 34 easily. The frost 34, as the window portion sinks through it, occupies the inner space defined by the window, and the frost height may be directly noted by the user by counting the calibrated lines 28 adjacent the lower edge of the window sides to the frost surface.

Figure 2:
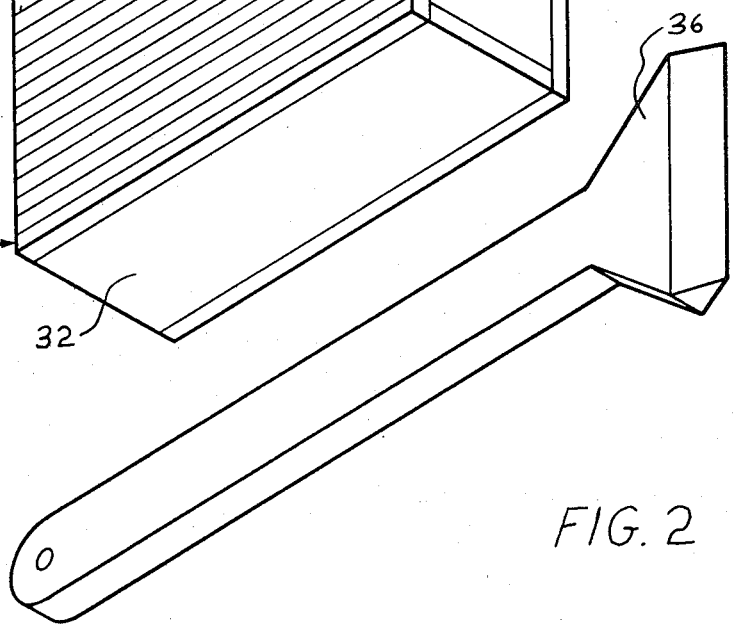
FIG. 2 is a pictorial view of a scraper implement to be used with the device shown in FIG. 1.

Following the height measurement of the frost, the frost within the inner space of the window portion 14 is pushed rearwardly through the entry opening 25 of the container portion 22 by using a scraper 36, shown in FIG. 2 or other suitable device. In FIG. 3, half of the frost within the window portion 14 is shown as being pushed into the container portion 22. The slanted rear plate 19 of the window portion is useful in the sliding of frost from the window into the container portion.

After all the frost within the window portion 14 has been placed into the container 22, the device is removed from the frost covered surface and the frost within the container is allowed to melt. At this time the device should be tilted in a position that places the rear bottom plate 32 downwardly so as to prevent the spilling of the water from the container 22. The height of the melt or water from the rear bottom plate 32 is then noted by the user by counting the calibrated lines 30 from the rear plate 32.

Figure 4:
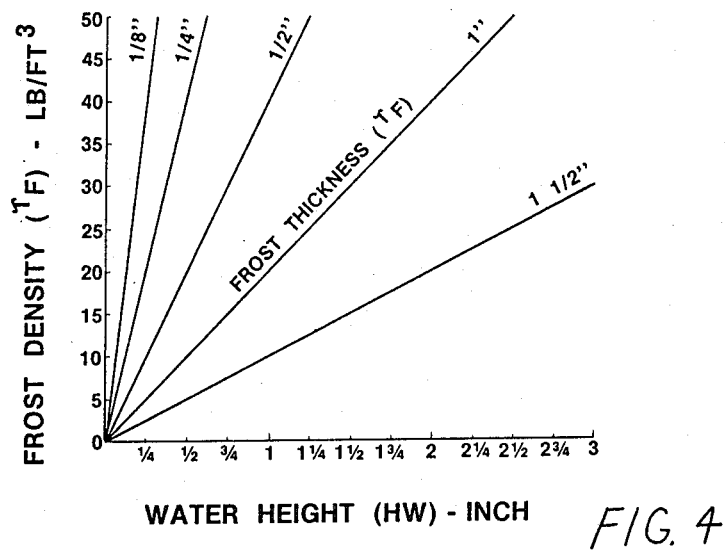
FIG. 4 is a graph appearing on the lower surface of the container portion of the device shown in FIG. 1.

A graph is shown in FIG. 4 which is affixed or etched on the outer surface of the bottom plate 24 of the container. The graph is derived from the mathematical relationships of container and window dimensions to correlate the water height as the abscissa axis and the frost density as the ordinate axis with various line plots of frost depth or thickness. The plot shown was derived from a window portion 14 that has an inside square length of three inches at its lower side edge and a container 22 with a length and width of three inches and a depth of one inch.

The device 12 is particularly useful for operation by a layman because it does not require specific calculations or knowledge of formulas to obtain a density reading or the use of special measurements on the frost surface. The user merely has to make two readings, and with those two readings read from the graph the density of the frost.

Modifications could be made to the device without departing from its essential characteristics.

I claim:

1. A device for determining the density and depth of frost on a surface, comprising:
    a unitary body having a forward open window portion adapted to be placed against the frost surface and adapted to have downward pressure applied thereto so as to cause it to sink readily to the underlying supporting surface whereby the frost will occupy the open space within the window;
    said unitary body having a rear container portion with a lower plate secured at a front end thereof to an upper edge of a rear part of the window portion;
    said rear container portion having a front entry opening above the lower plate of said rear container portion and rearward of the upper edge of said window portion for receiving the frost scraped from the open window;
    calibrated lines along a side of the open window portion to enable an observer to note the depth of the frost;
    calibrated lines along a side of the container portion to enable an observer to note the height of the water therein, water resulting only from the melting of said frost therein scraped from the window portion; and
    a graph on another side of the rear container portion to enable an observer to correlate the depth of the frost and the height of the water noted to the density of the frost.

2. A device as defined by claim 1 wherein said unitary body is made of transparent material to enable the frost depth and water height determinations using the calibrated lines to be easily made.

3. A device as defined by claim 2 wherein said open window portion is constructed of planar sides arranged in a substantially rectangular configuration, the sides adjacent their lower edges being beveled to form a sharp lower edge.

4. A device as defined by claim 3 wherein:
    said calibrated lines along the sides of the window portion are parallel to their bottom edges and spaced in equal increments therefrom;
    said calibrated lines along a side of the container portion are parallel to the rear of the container portion and spaced in equal increments therefrom.

5. A device as defined by claim 4 wherein said graph depicts water height values along an abscissa axis, frost density values along an ordinate axis, and various line plots therebetween of frost depth.

6. A device as defined by claim 3 wherein said rear part of the window portion is the rear planar side and said rear planar side is slanted outwardly from its lower to upper edges to enable the frost occupying the open window to be easily slid into the front entry opening of said rear container portion.

7. A device for determining the density and thickness of frost or the like on a surface comprising:
    a unitary body having a forward portion with plate sides defining an open rectangular window configuration;
    said unitary body having a rear portion in the form of a container having a front entry opening;
    said container having a lower plate secured at a front end thereof to a rear plate side of said forward portion whereby said front entry opening of the container is above the rear plate side of said forward portion;
    said plate sides of said forward portion having their lower outer surface beveled inwardly to form sharp bottom edges;
    the rear plate side of said forward portion slanting outwardly from its lower edge to its upper edge;
    calibrated lines along the plate sides of said front portion, said calibrated lines parallel to bottom edges of the plate sides;
    said container having a plate with calibrated lines parallel to its rear plate; and
    another plate of said container have a graph correlating the height of water in said container resulting only from the melting of frost of the like moved therein from said open window and the height of the frost or the like within said open window to the density of said frost or the like.

* * * * *